United States Patent
Tu et al.

(10) Patent No.: US 10,424,736 B2
(45) Date of Patent: Sep. 24, 2019

(54) AGING TEST SYSTEM FOR DISPLAY PANEL AND AGING TEST METHOD FOR THE SAME

(71) Applicant: Shenzhen China Star Optoelectronics Technology Co., Ltd., Shenzhen, Guangdong (CN)

(72) Inventors: Aiguo Tu, Guangdong (CN); Chun-Hsiung Fang, Guangdong (CN); Tsung-yuan Wu, Guangdong (CN); Jinchuan Li, Guangdong (CN); Liang Jiang, Guangdong (CN); Feng Wei, Guangdong (CN)

(73) Assignee: Shenzhen China Star Optoelectronics Technology Co., Ltd, Shenzhen, Guangdong (CN)

( * ) Notice: Subject to any disclaimer, the term of this patent is extended or adjusted under 35 U.S.C. 154(b) by 0 days.

(21) Appl. No.: 15/577,012

(22) PCT Filed: Aug. 17, 2017

(86) PCT No.: PCT/CN2017/097745
§ 371 (c)(1),
(2) Date: Nov. 27, 2017

(87) PCT Pub. No.: WO2018/232924
PCT Pub. Date: Dec. 27, 2018

(65) Prior Publication Data
US 2019/0013473 A1 Jan. 10, 2019

(30) Foreign Application Priority Data
Jun. 23, 2017 (CN) .......................... 2017 1 0485956

(51) Int. Cl.
*H01L 51/00* (2006.01)
*G01N 21/95* (2006.01)
(Continued)

(52) U.S. Cl.
CPC ......... *H01L 51/0031* (2013.01); *G01N 21/27* (2013.01); *G01N 21/95* (2013.01); *H01L 51/56* (2013.01); *H01L 2251/562* (2013.01)

(58) Field of Classification Search
CPC ................. H01L 51/0031; H01L 51/56; H01L 2251/562; G01N 21/27; G01N 21/95
See application file for complete search history.

(56) References Cited

U.S. PATENT DOCUMENTS 6,916,221 B2 7/2005 Kaltenbach et al.
8,427,170 B2 4/2013 Morimoto et al.
(Continued)

FOREIGN PATENT DOCUMENTS

CN 101153886 A 4/2008
CN 101349728 A 1/2009
(Continued)

*Primary Examiner* — Dominic J Bologna
(74) *Attorney, Agent, or Firm* — Andrew C. Cheng

(57) ABSTRACT

An aging test system and method are disclosed. An aging test system includes a vacuum chamber provided with an aging device for aging a display panel; a lighting mechanism electrically connected to the display panel for lighting up the display panel; at least one spectrometer for detecting a color coordinate and a brightness of the display panel; at least one camera for detecting a dark spot defect of sub-pixels of the display panel. Accordingly, the present invention can save the inspection time, increase the inspection efficiency and save the inspection device in order to reduce the inspection cost.

16 Claims, 1 Drawing Sheet

(51) Int. Cl.
  *G01N 21/27* (2006.01)
  *H01L 51/56* (2006.01)

(56) References Cited

U.S. PATENT DOCUMENTS

| | | | |
|---|---|---|---|
| 2004/0097160 A1* | 5/2004 | Kaltenbach | H01L 51/56 445/3 |
| 2006/0094321 A1* | 5/2006 | Maeda | H01L 51/56 445/6 |
| 2010/0225770 A1* | 9/2010 | Morimoto | G09G 3/006 348/189 |
| 2011/0130981 A1 | 6/2011 | Chaji et al. | |
| 2013/0277617 A1* | 10/2013 | Pan | H01L 51/0043 252/500 |
| 2014/0346475 A1* | 11/2014 | Cho | H01L 27/326 257/40 |
| 2015/0114297 A1* | 4/2015 | Kawato | C23C 14/24 118/726 |
| 2016/0088779 A1* | 3/2016 | Ahn | H01L 51/56 29/464 |
| 2016/0247429 A1* | 8/2016 | Li | H01L 51/0031 |

FOREIGN PATENT DOCUMENTS

| | | |
|---|---|---|
| CN | 201247352 Y | 5/2009 |
| CN | 102368827 A | 3/2012 |
| CN | 102402944 A | 4/2012 |
| CN | 103529571 A | 1/2014 |
| CN | 104157585 A | 11/2014 |
| JP | 2009139129 A | 6/2009 |
| KR | 100926048 B | 11/2009 |

* cited by examiner

AGING TEST SYSTEM FOR DISPLAY PANEL AND AGING TEST METHOD FOR THE SAME

BACKGROUND OF THE INVENTION

1. Field of the Invention

The present invention relates to a display technology field, and more particularly to an aging test system for display panel and an aging test method for the same.

2. Description of Related Art

An organic light-emitting diode (OLED) has features of self-luminous, no backlight, high contrast, thin thickness, wide viewing angle, fast response, can be used for flexible panel, wide temperature range application, simple structures and processes such that the OLED is regarded as an emerging application technology for a next generation flat display.

The OLED is formed by a cathode and an anode, and function layers disposed between the cathode and the anode. Wherein, the function layers includes a HIL (Hole injection layer), a HTL (Hole transport layer), a EML (Light-emitting layer), a ETL (Electron transport layer) and a EIL (Electron injection layer).

In order to extend the application range of the organic light-emitting diode, and commercialize the organic light-emitting diode, technologies for increasing the efficiency of the organic light-emitting diode and decreasing the driving voltage are developed.

The OLED has been widely applied in a small to middle size display panel. A large-sized OLED TV has started to be commercialized. Comparing to the small to middle size display panel, because a large OLED TV has a large area, a yield is difficult to be improved. When manufacturing the large OLED TV, defects such as dark spots and bright spots are easily to be generated. In a low grayscale level, a mura phenomenon generated by the dark spots is more obvious. An on-line aging process is required in the OLED manufacturing processes, and through the aging process to reduce the defects of the dark spots in order to increase the yield of the large size OLED panel. In the conventional art, after an OLED display panel passing through an on-line aging chamber, the OLED display panel is delivered to an IVL (current-voltage-bright) lighting chamber to inspect the aging effect. After screening, entering into a packaging process. However, the above processes require a longer inspection time, and two chambers of the aging chamber and the light chamber are required so that the device cost is high.

SUMMARY OF THE INVENTION

The main technology problem solved by the present invention is to provide an aging test system for display panel and method for the same, which can save the inspection time, increase the inspection efficiency and save the inspection device in order to reduce the inspection cost.

In order to solve the above technology problem, a technology solution adopted by the present invention is: providing an aging test system for display panel, comprising: a vacuum chamber provided with an aging device for aging a display panel; a lighting mechanism electrically connected to the display panel for lighting up the display panel, the lighting mechanism includes a connection rod and a pin, wherein, one terminal of the connection rod is disposed at an inner wall of the vacuum chamber, and the other terminal of the connection rod is connected to the pin, and the pin is used for electrically connecting to the display panel; at least one spectrometer located at an optical path of a light emitted from the display panel for detecting a color coordinate and a brightness of the display panel; at least one camera located at the optical path of the light emitted from the display panel for detecting a dark spot defect of sub-pixels of the display panel; wherein, the vacuum chamber is provided with the lighting mechanism, the at least one spectrometer and the at least one camera, and a side of the vacuum chamber is provided with a gas pipeline for inputting one of nitrogen and air.

In order to solve the above technology problem, another technology solution adopted by the present invention is: an aging test system for display panel, comprising: a vacuum chamber provided with an aging device for aging a display panel; a lighting mechanism electrically connected to the display panel for lighting up the display panel; at least one spectrometer located at an optical path of a light emitted from the display panel for detecting a color coordinate and a brightness of the display panel; at least one camera is located at the optical path of the light emitted from the display panel for detecting a dark spot defect of sub-pixels of the display panel; wherein, the vacuum chamber is provided with the lighting mechanism, the at least one spectrometer and the at least one camera.

In order to solve the above technology problem, another technology solution adopted by the present invention is: an aging test method for display panel, comprising steps of: lighting a display panel up; and detecting a color coordinate and a brightness of the display panel, and inspecting a dark spot defect of sub-pixels of the display panel.

The beneficial effect of the present invention is: comparing to the conventional art, the present invention provides an aging test system for display panel, comprising: a vacuum chamber provided with an aging device for aging a display panel; a lighting mechanism electrically connected to the display panel for lighting up the display panel; at least one spectrometer located at an optical path of a light emitted from the display panel for detecting a color coordinate and a brightness of the display panel; at least one camera is located at the optical path of the light emitted from the display panel for detecting a dark spot defect of sub-pixels of the display panel; wherein, the vacuum chamber is provided with the lighting mechanism, the at least one spectrometer and the at least one camera. Accordingly, the present invention disposes the lighting mechanism, the spectrometer and the camera in the vacuum chamber such that an aging process and an aging inspection can be directly finished in the vacuum chamber so that the present invention can save the inspection time, increase the inspection efficiency and save the inspection device in order to reduce the inspection cost.

BRIEF DESCRIPTION OF THE DRAWINGS

In order to more clearly illustrate the technical solution in the present invention or in the prior art, the following will illustrate the figures used for describing the embodiments or the prior art. It is obvious that the following figures are only some embodiments of the present invention. For the person of ordinary skill in the art without creative effort, it can also obtain other figures according to these figures.

DETAILED DESCRIPTION OF THE PREFERRED EMBODIMENT

The following content combines with the drawings and the embodiment for describing the present invention in detail. It is obvious that the following embodiments are only some embodiments of the present invention. For the person of ordinary skill in the art without creative effort, the other embodiments obtained thereby are still covered by the present invention.

Figure 1:
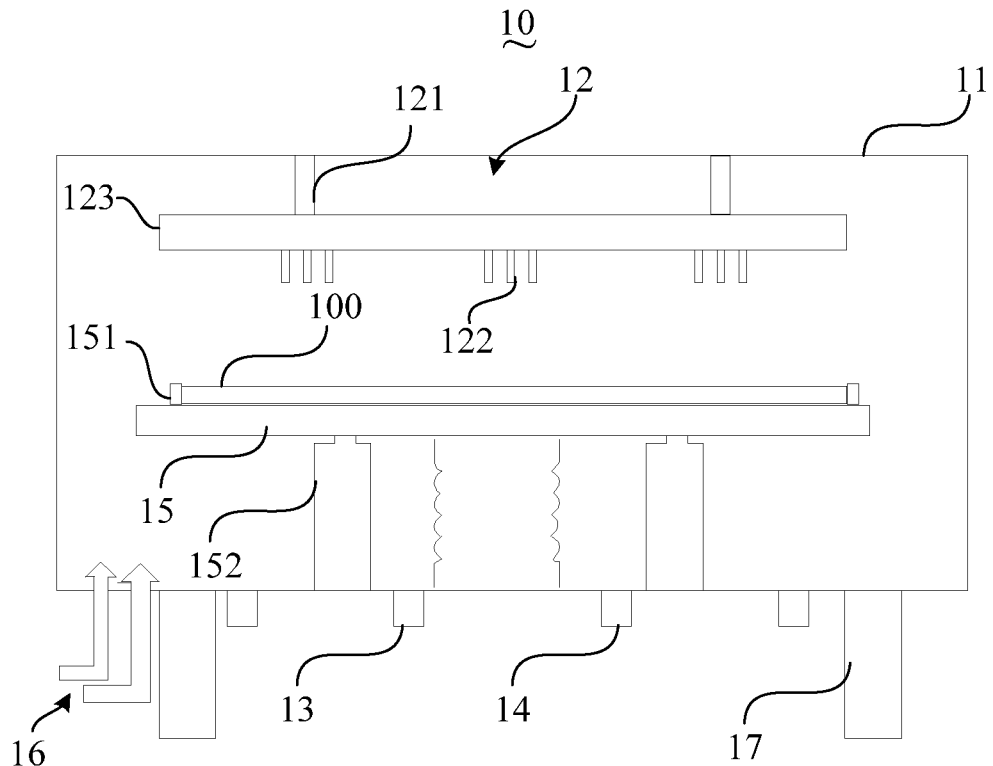
FIG. 1 is a schematic diagram of an aging test system for a display panel according to an embodiment of the present invention.

With reference to FIG. 1, and FIG. 1 is a schematic diagram of an aging test system for a display panel according to an embodiment of the present invention. As shown in FIG. 1, the aging test system 10 of the present invention includes a vacuum chamber 11, a lighting mechanism 12, at least one spectrometer 13 and at least one camera 14.

Wherein, the vacuum chamber 11 is provided with an aging device (not shown) for aging a display panel 100, and the vacuum chamber 11 is provided with the lighting mechanism 12, the spectrometer 13 and the camera 14.

Specifically, to speed up aging, a side of the vacuum chamber 11 is provided with a gas pipeline 16 for inputting one of nitrogen and air. For accelerating inputting a gas, two or above gas pipelines 16 can be provided. As shown in FIG. 1, two gas pipelines 16 are provided. Wherein, the air includes anyone of a compressed air and a clean air. Wherein, the compressed air is an air that contains water, and the clean air is an air that no oil and no particles are contained, and no requirement for water.

The aging test system 10 further includes a supporting element 17 for supporting the vacuum chamber 11.

In another embodiment, the gas can be preheated. Then, inputting the heated gas into the vacuum chamber 11 in order to further accelerate the aging of the display panel 100.

The lighting mechanism 12 is electrically connected to the display panel 100 for lighting up the display panel 100. Specifically, the lighting mechanism 12 includes a connection rod 121 and a pin 122. One terminal of the connection rod 121 is disposed at an inner wall of the vacuum chamber 11, and the other terminal of the connection rod 121 is connected to the pin 122. More specifically, the lighting mechanism 12 further includes a connection board 123. The pin 122 is disposed at the connection board 123, and the other terminal of the connection rod 121 is electrically connected to the pin 122 through the connection board 123. The pin 122 is used for electrically connecting to the display panel 100.

In the present embodiment, the number of the pins 122 is multiple, and being evenly divided into preset groups, and disposed at preset locations of the connection board 123. For example, as shown in FIG. 1, the multiple pins 122 are divided into three groups, and each group includes three pins. When performing a lighting test, the pins 122 are connected to the display panel 100 through pin pads on the display panel 10o, and the display panel 100 is lighted up. Wherein, the way to light up the display panel 100 is multiple. For example, pixels of the display panel 100 can be divided into multiple regions, the lighting mechanism 12 sequentially lights up the multiple regions through the pins 122 or simultaneously lights up the multiple regions.

The at least one spectrometer 13 is located at an optical path of a light emitted from the display panel 100 for detecting a color coordinate and a brightness of the display panel 100. That is, the spectrometer 13 directly detects the color coordinates and brightness of the display panel 100. Through detecting the color coordinates and brightness of each of three primary colors, a color gamut of the display panel 100 is obtained for using as a judgment criteria of an aging effect of the display panel 100. In the present embodiment, using NTSC gamut standard as an example, if the gamut of the display panel 100 obtained through the color coordinates and brightness is less than 72%, the display panel 100 is unqualified.

The at least one camera 14 is located at the optical path of the light emitted from the display panel 100 for detecting a dark spot defect of sub-pixels of the display panel 100. Specifically, after the lighting mechanism 12 lights the display panel 100 up, the camera 14 take a picture for evidence to the display panel 100. Then, the present invention inspects if the sub-pixel of the display panel 100 exists the dark spot defect, and calculating the number of the dark spot defects. Usually, calculating the number of the dark spot defects when lighting up a monochromatic image. For example, through respectively lighting up three colors of RGB or four colors of RGBW, calculating the number of the dark spot defects. Wherein, a dark spot threshold is preset, and if the number of the dark spot defects is greater than dark spot threshold, the display panel 100 is determined to be unqualified.

In the present embodiment, the number of the spectrometer 13 and the number of the camera 14 are both two. The spectrometers 13 and the cameras 14 are alternately disposed at the optical path of the light emitted from the display panel 100. For example, from a left and a right, respectively providing a spectrometer 13, a camera 14, a spectrometer 13 and a camera 14.

In the present embodiment, the spectrometer 13 and the camera 14 are disposed separately at outside of the vacuum chamber 11. Specifically, the vacuum chamber 11 receives the display panel 100, the lighting mechanism 12 and the supporting table 15. Besides, an outside surface of the vacuum chamber 11 is provided with the spectrometer 13 and the camera 14.

In the present embodiment, the aging test system 10 further includes a supporting table 15 for supporting the display panel 100. In order to strengthen a supporting function, below the supporting table 15, three supporting rods 152 are provided. On the supporting table 15, an alignment system 151 is further provided. The alignment system 151 is used for adjusting the position of the display panel 100 such that the display panel 100 is corresponding to the pins 122, the spectrometers 13 and the camera 14 such that the pins 122 is convenient to be electrically connected to the display panel 100 and the spectrometer 13 and the camera 14 is convenient for inspecting the display panel 100.

As described above, in the present invention, the spectrometers 13 and the camera 14 are integrally formed outside the vacuum chamber 11, and the lighting mechanism 12 and the aging device are disposed inside the vacuum chamber 11. Accordingly, a lighting test can be directly finished in the vacuum chamber 11, and obtaining the colors of the display panel and the dark spot defects of the sub-pixels so that the aging process and the aging inspection of the display panel can be finished at the same time so that the present invention can save the inspection time, increase the inspection efficiency and save the inspection device in order to reduce the inspection cost. Wherein, the display panel 100 can be an OLED display panel or a LCD display panel.

The embodiment of the present invention also provides an aging test method for a display panel, the aging test method is suitable for the aging test system describe above. Specifically, referring to FIG. 2.

Figure 2:
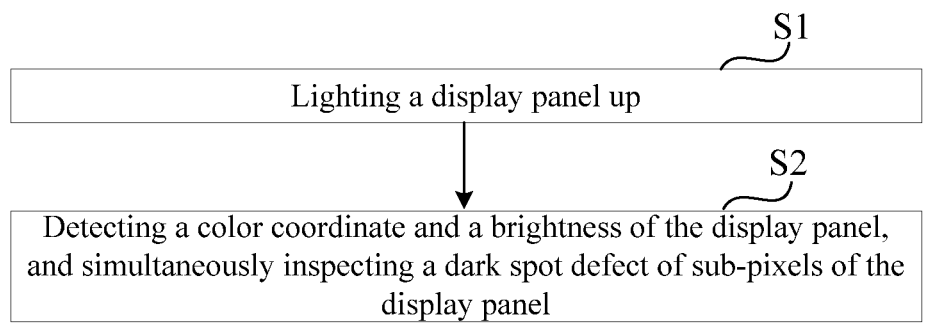
FIG. 2 is a flow chart of an aging test method for display panel according to an embodiment of the present invention.

As shown in FIG. 2, the aging test method for the embodiment of the present invention includes following steps:

Step S1: lighting a display panel up.

Step S2: detecting a color coordinate and a brightness of the display panel, and simultaneously inspecting a dark spot defect of sub-pixels of the display panel. The specific operation principle is described above, no more repeating.

In the present embodiment, using NTSC gamut standard as an example, if the gamut of the display panel 100 obtained through the color coordinates and brightness is less than 72%, the display panel 100 is unqualified.

Wherein, a dark spot threshold is preset, and if the number of the dark spot defects is greater than dark spot threshold, the display panel 100 is determined to be unqualified.

Wherein, in to speed up aging, the present embodiment further provides one of nitrogen and air. The air includes anyone of a compressed air and a clean air. Wherein, the compressed air and the clean air are as described above, no more repeating.

In another embodiment, the gas can be preheated. Then, inputting the heated gas into the vacuum chamber in order to further accelerate the aging of the display panel.

In summary, in the present invention, the aging process and the aging inspection of the display panel are formed at the same time so that the present invention can save the inspection time, increase the inspection efficiency and save the inspection device in order to reduce the inspection cost.

The above embodiments of the present invention are not used to limit the claims of this invention. Any use of the content in the specification or in the drawings of the present invention which produces equivalent structures or equivalent processes, or directly or indirectly used in other related technical fields is still covered by the claims in the present invention.

What is claimed is:

1. An aging test system for display panel, comprising:
   a vacuum chamber provided with an aging device for aging a display panel;
   a lighting mechanism electrically connected to the display panel for lighting up the display panel, the lighting mechanism includes a connection rod and a pin, wherein, one terminal of the connection rod is disposed at an inner wall of the vacuum chamber, and the other terminal of the connection rod is connected to the pin, and the pin is used for electrically connecting to the display panel;
   at least one spectrometer located at an optical path of a light emitted from the display panel for detecting a color coordinate and a brightness of the display panel; and
   at least one camera located at the optical path of the light emitted from the display panel for detecting a dark spot defect of sub-pixels of the display panel;
   wherein, the vacuum chamber is provided with the lighting mechanism, the at least one spectrometer and the at least one camera, and a side of the vacuum chamber is provided with a gas pipeline for inputting one of nitrogen and air.

2. The aging test system according to claim 1, wherein, the aging test system further includes a supporting table for supporting the display panel.

3. The aging test system according to claim 2, wherein, the supporting table is provided with an alignment system for adjusting a position of the display panel.

4. The aging test system according to claim 2, wherein, the vacuum chamber is used for receiving the display panel, the lighting mechanism and the supporting table, and the at least one spectrometer and the least one camera are located at an outside surface of the vacuum chamber.

5. The aging test system according to claim 4, wherein, the at least one spectrometer and the least one camera are alternately disposed at the outside surface of the vacuum chamber.

6. The aging test system according to claim 1, wherein, the aging test system further includes a supporting element for supporting the vacuum chamber.

7. An aging test system for display panel, comprising:
   a vacuum chamber provided with an aging device for aging a display panel;
   a lighting mechanism electrically connected to the display panel for lighting up the display panel;
   at least one spectrometer located at an optical path of a light emitted from the display panel for detecting a color coordinate and a brightness of the display panel;
   at least one camera located at the optical path of the light emitted from the display panel for detecting a dark spot defect of sub-pixels of the display panel;
   wherein, the vacuum chamber is provided with the lighting mechanism, the at least one spectrometer and the at least one camera;
   wherein the lighting mechanism comprises a connection rod and a pin, wherein one terminal of the connection rod is disposed at an inner wall of the vacuum chamber, and the other terminal of the connection rod is connected to the pin, and the pin is used for electrically connecting to the display panel.

8. The aging test system according to claim 7, wherein, the aging test system further includes a supporting table for supporting the display panel.

9. The aging test system according to claim 8, wherein, the supporting table is provided with an alignment system for adjusting a position of the display panel.

10. The aging test system according to claim 8, wherein, the vacuum chamber is used for receiving the display panel, the lighting mechanism and the supporting table, and the at least one spectrometer and the least one camera are located at an outside surface of the vacuum chamber.

11. The aging test system according to claim 10, wherein, the at least one spectrometer and the least one camera are alternately disposed at the outside surface of the vacuum chamber.

12. The aging test system according to claim 7, wherein, a side of the vacuum chamber is provided with a gas pipeline for inputting one of nitrogen and air.

13. The aging test system according to claim 7, wherein, the aging test system further includes a supporting element for supporting the vacuum chamber.

14. The aging test system according to claim 7, wherein the at least one spectrometer and the at least one camera are alternately disposed at the optical path of the light emitted from the display panel and separately disposed outside of the vacuum chamber.

15. An aging test method for display panel, comprising steps of:
   lighting, by a lighting mechanism, a display panel up; and
   detecting, by at least one spectrometer, a color coordinate and a brightness of the display panel, and simultaneously detecting, by at least one camera, a dark spot defect of sub-pixels of the display panel;

wherein the lighting mechanism is electrically connected to the display panel, and at least one spectrometer and at least one camera are located at an optical path of a light emitted from the display panel;

wherein the lighting mechanism comprises a connection rod and a pin, wherein one terminal of the connection rod is disposed at an inner wall of the vacuum chamber, and the other terminal of the connection rod is connected to the pin, and the pin is used for electrically connecting to the display panel.

16. The aging test method according to claim 15, wherein, the method further includes a step of providing at least one of nitrogen and air.

* * * * *